United States Patent
Epstein et al.

(10) Patent No.: US 6,575,205 B2
(45) Date of Patent: Jun. 10, 2003

(54) DIRECT DUAL FILLING DEVICE FOR SEALING AGENTS

(75) Inventors: Gordon Howard Epstein, Fremont, CA (US); Alan Plyley, Clearlake Park, CA (US); Russell James Redmond, Goleta, CA (US)

(73) Assignee: Baxter International, Deerfield, IL (US)

( * ) Notice: Subject to any disclaimer, the term of this patent is extended or adjusted under 35 U.S.C. 154(b) by 3 days.

(21) Appl. No.: 09/731,488

(22) Filed: Dec. 7, 2000

(65) Prior Publication Data

US 2002/0072714 A1 Jun. 13, 2002

(51) Int. Cl.[7] .............................................. B65B 31/00
(52) U.S. Cl. ..................... 141/42; 604/191; 604/195; 128/764
(58) Field of Search ................. 604/191, 195, 604/186, 190; 128/764; 433/81; 137/112; 141/42

(56) References Cited

U.S. PATENT DOCUMENTS

| | | | | |
|---|---|---|---|---|
| 3,774,654 A | * | 11/1973 | Hjermstad | 141/42 |
| 4,690,165 A | * | 9/1987 | Leytes et al. | 137/112 |
| 4,856,567 A | | 8/1989 | Cosmai | |
| 4,883,483 A | | 11/1989 | Lindmayer | |
| 4,902,281 A | * | 2/1990 | Avoy | 604/191 |
| 5,171,146 A | * | 12/1992 | Guerci | 433/81 |
| 5,195,985 A | * | 3/1993 | Hall | 604/195 |
| 5,297,561 A | * | 3/1994 | Hulon | 128/764 |
| 5,445,631 A | | 8/1995 | Uchida | |
| 5,478,323 A | | 12/1995 | Westwood et al. | |
| 5,656,035 A | | 8/1997 | Avoy | |
| 5,788,662 A | | 8/1998 | Antanavich et al. | |
| 5,827,262 A | | 10/1998 | Neftel et al. | |
| 5,901,883 A | | 5/1999 | Ritsche | |
| 6,063,297 A | | 5/2000 | Antanavich et al. | |

FOREIGN PATENT DOCUMENTS

| | | |
|---|---|---|
| WO | 8904676 | 6/1989 |
| WO | 9001959 | 3/1990 |
| WO | 9406487 | 3/1994 |
| WO | 9917833 | 4/1999 |
| WO | 9930769 | 6/1999 |
| WO | 9932155 | 7/1999 |
| WO | 9962588 | 12/1999 |

* cited by examiner

*Primary Examiner*—Henry Bennett
(74) *Attorney, Agent, or Firm*—Oppenheimer Wolff & Donnelly; Brian Swienton

(57) ABSTRACT

A method and apparatus for filling a syringe-type applicator having multiple material reservoirs are disclosed. The method and apparatus permits the individual component reservoirs to be simultaneously filled without risk of contamination or unintentional component mixing. The method and apparatus are particularly useful in the preparation and delivery of multiple component tissue sealants such a fibrinogen adhesive compositions.

21 Claims, 5 Drawing Sheets

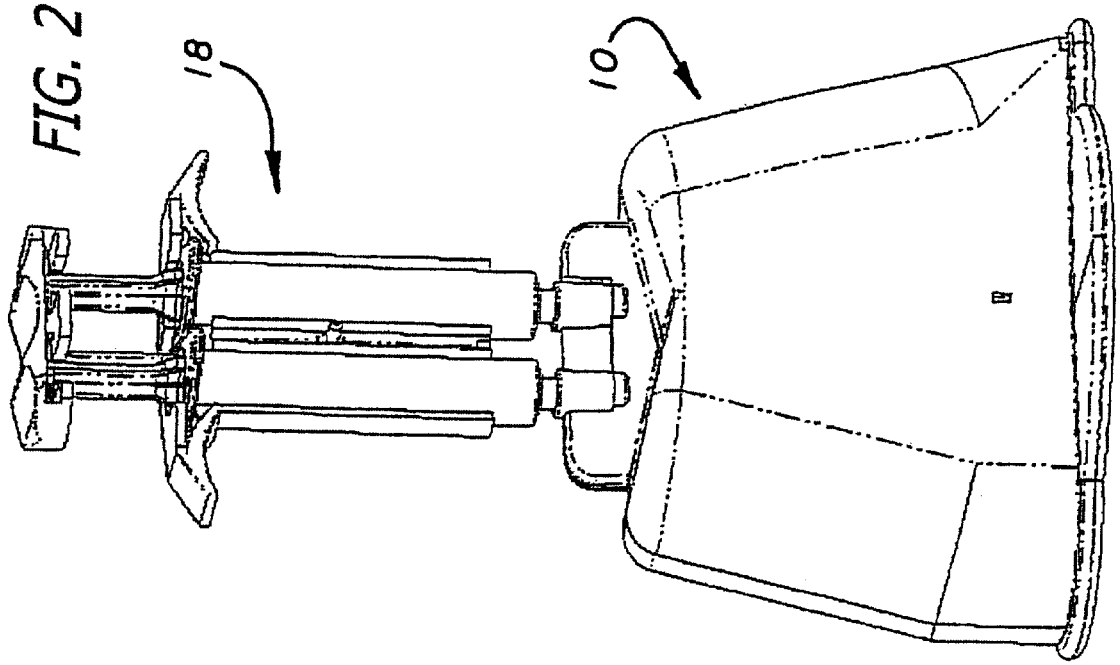
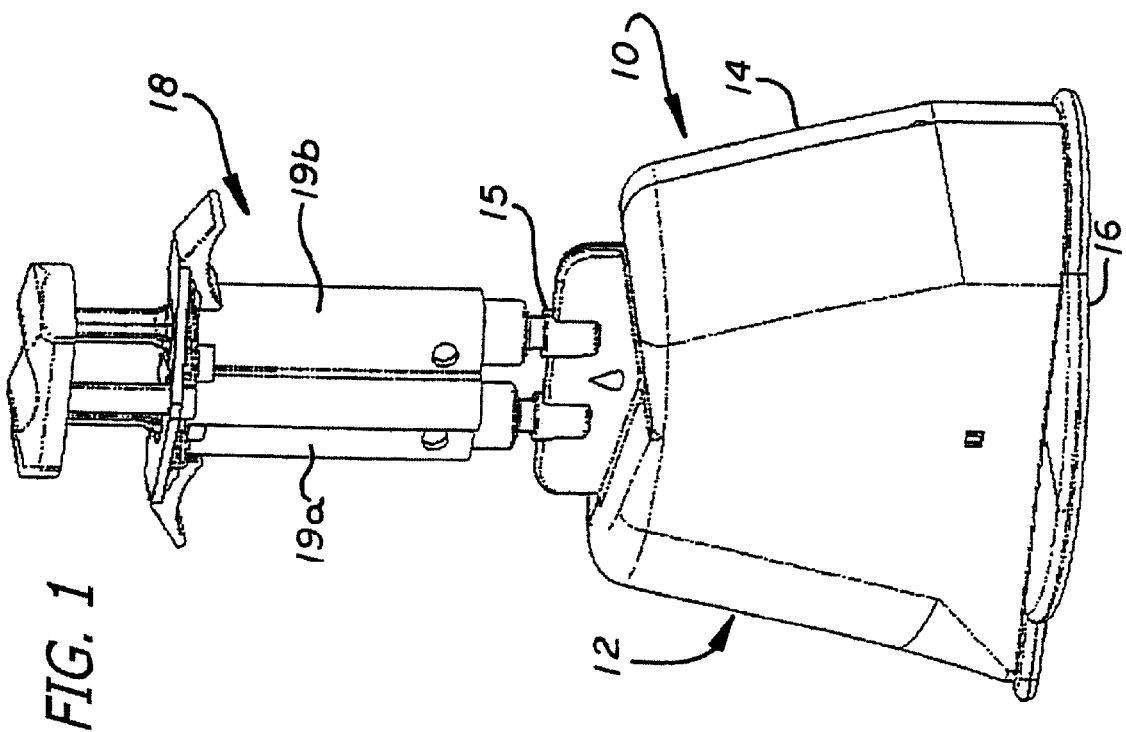

DIRECT DUAL FILLING DEVICE FOR SEALING AGENTS

REFERENCE TO RELATED APPLICATIONS

This application discloses subject matter related to our co-pending U.S. Continuation-In-Part patent application Ser. No. 09/456,728, filed Dec. 8, 1999, which claims priority from U.S. patent application Ser. No. 09/307,056 May 7, 1999, which claims priority from United States Provisional Application No. 60/087,856 filed Jun. 3, 1998, all naming Gordon H. Epstein as first inventor. The disclosures of the aforementioned United States patent applications, "the above applications" are hereby incorporated herein by reference thereto.

FIELD OF THE INVENTION

The present invention relates to a filling device for an syringe applicator which applies multiple fluid sealant components to a work surface and is particularly, although not exclusively, useful for applying tissue sealant components to biological tissue to effect hemostasis or achieve other therapeutic results. More particularly, it relates to a dual compartment enclosed direct filling device for a hand-held applicator.

BACKGROUND OF THE INVENTION

The use of tissue sealants and other biological materials is an important emerging surgical technique, well adapted for the operating room or field environments such as the doctor's office or mobile medical units. Preferred sealants include fibrin sealants which are formed from blood plasma components and comprise, on the one hand, a first component containing fibrinogen and Factor XIII and, on the other hand, a second component which usually includes thrombin, and calcium ions. The fibrinogen is capable of a polymerizing and being cross-linked to form a solid fibrin clot when the components are mixed. The necessary additional factors to simulate relevant portions of the natural blood coagulation cascade are suitably distributed between the fibrinogen and thrombin components.

Antanavich et al. U.S. Pat. No. 5,585,007, whose disclosure and references are hereby incorporated herein by reference thereto, provides an extensive discussion of the literature relating to fibrinogen sealant preparation (column 1, line 20 to column 4, line 62) and applicators (column 4 line 62 to column 5, line 14), as well as a bibliography, (columns 6–10) and is a helpful guide to the teachings of prior workers in the field.

Depending upon the potency of the particular formulations employed, coagulation of the sealant may take place very rapidly, yielding a gel within perhaps 10 or 20 seconds. Though often very desirable for surgical reasons, such fast-acting properties present potential problems of fouling or clogging. These problems must be overcome in devising suitable applicators, methods of application, and devices suitable for filling said applicators.

A popular manually operable applicator for such two-component sealants employs a dual syringe construction wherein two syringes, connected by a yoke, each provide a reservoir for one of the components. In most prior devices, the sealant components are discharged in separate streams and mixed external of the applicator. Such applicators are similar in principle to household epoxy glue applicators commonly available in hardware stores.

Until May of 1998, when the FDA first approved such products, fibrin sealants were not commercially available in the US. Therefore, the use of fibrin sealants was limited to supplies produced within the clinic, which were not subject to FDA control.

Current methods of filling biological glue applicators can be complicated and time consuming. As taught in U.S. Pat. No. 5,266,877, issued to Epstein, and in our assignee's international application PCT/US98/07846, components of the sealant can be placed in separate compartments in a flat filler tray for transfer to an applicator. Though useful as a device to permit rapid and reliable filling of a dual syringe applicator at the point of use, such filler trays are not suitable for external storage of the sealant components. This process can be time consuming and it requires a significant degree of care to efficiently transfer the sealant to the applicator. Also, a small amount of sealant will be left in the tray, and it is thus wasted. Furthermore the transfer of sealant components to multiple storage containers raises the likelihood members in which the sealants will gather bio-burden, and bacteria, which can threaten the sterility of the sealant.

Following FDA approval, however, fibrin sealants are now commercially available in the US. This availability has created a need for an effective and efficient device useful for transferring the components of the sealant, from commercially available or standardized, container-like storage containers, into an applicator.

There is accordingly a need for a device which can effectively deliver, in a sterile environment, multiple sealant components directly from their storage containers to a syringe applicator.

SUMMARY OF THE INVENTION

The present invention solves the problem of effectively delivering multiple sealant components directly from commercially available or standardized storage containers, for example, containers, to an applicator while allowing the use of the entire fill device within a sterile field.

In one aspect, the invention provides a direct dual filling device for multiple sealant components of a liquid sealant, at least two of the components being complementary one to the other and capable of polymerizing when mixed. The direct dual filling device comprises a body having a plurality of inlet ports connected to drawing tubes which pierce the protective covering of commercially available containers, the containers containing the sealant components. The device also includes a housing member which sealably mounts onto a base, thereby enclosing the containers within the structure and allowing the device to be brought into a sterile field. The housing member and slanted container supports hold the containers in a tilted position within the receiving aperture. This feature allows the drawing tubes to extract virtually all of the fluid contained within the containers. The device can be attached to a syringe applicator with keying such that when the plunger of the syringe applicator is retracted, fluid is drawn from each respective container to the proper reservoir contained within the syringe applicator.

The invention enables multiple sealant components to be directly delivered from their commercially available containers into a syringe applicator without significant risk of contamination of the sealant components, while minimizing waste of the sealant components. The different sealant components are delivered directly from their containers into separate individual reservoirs within the syringe applicator, thereby preventing coagulation of the sealant components. Once the housing member of the device is guided onto the containers and mounted onto the base, the entire device can be brought into the sterile environment.

BRIEF DESCRIPTION OF THE DRAWINGS

The apparatus of the present invention will be explained in more detail by way of the accompanying drawings, wherein:

FIG. 1 show a side elevation view of the present invention attached to a syringe-type applicator;

FIG. 2 shows an alternate side view of the present invention attached to a syringe-type applicator;

DETAILED DESCRIPTION OF THE INVENTION

Figure 3:
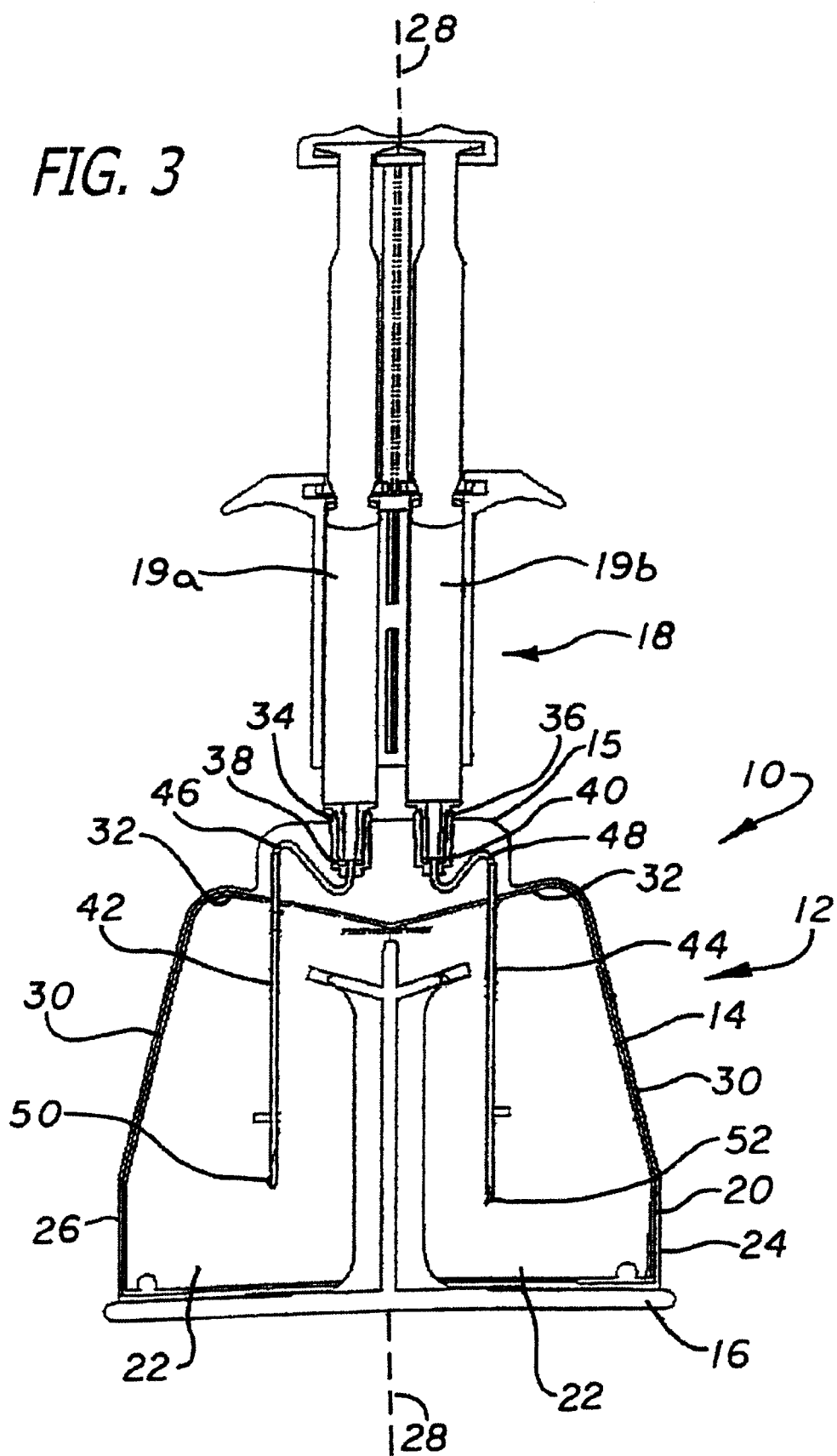
FIG. 3 shows a cross-sectional view of the present invention attached to a syringe-type applicator.

Disclosed herein is a detailed description of various illustrated embodiments of the invention. This description is not to be taken in a limiting sense, but is made merely for the purpose of illustrating the general principles of the invention. The section titles and overall organization of the present detailed description are for the purpose of convenience only and are not intended to limit the present invention.

The direct dual filling device of the present invention is used in conjunction with a syringe-type sealant applicator, to dispense a tissue sealant thereby effecting hemostasis or achieving other therapeutic results. The direct dual filling device of the present invention is designed to permit the withdrawal of fluid from at least one commercially available fluid container and fill a syringe-type applicator, for example, the DUPLOJECT™ syringe-type applicator manufactured by the Baxter Corporation. As those skilled in the art will appreciate, the present invention permits the controlled withdrawal of fluid from the fluid container and filling of at least one material reservoir of the syringe-type applicator. It is anticipated as being within the scope of the present invention to produce a direct dual filling device capable of functionally coupling with a plurality of syringe-type applicators in a plurality of sizes.

Referring to FIGS. 1 and 2 of the drawings, the direct dual filling device 10 comprises a body 12, a housing member 14 and a collar 15 which is adapted to fit a syringe-type applicator 18, and a separable base portion 16. The inventive device is preferably constructed out of a clear thermoplastic material such as polycarbonate, polystyrene, polypropylene, polytetrafluoroethylene, acrylonitrile butadiene-styrene or acrylic, however any suitable material may be used.

Applicator 18 preferably has at least one fluid reservoir for holding and controllably dispensing reactable fluids, the fluid reservoir being connected to a syringe by a fluid conduit (not shown). As shown in FIG. 1, the illustrated embodiment of the applicator 18 has two fluid reservoirs 19a and 19b for holding and controllably dispensing reactable fluids, with each of the fluid reservoirs being connected to the syringe by fluid conduits (not shown). The applicator 18 is of the type primarily used for applying multiple fluid sealant components to biological tissue to effect hemostasis or achieve other therapeutic results. However the inventive filling device can be adapted to fit applicators having a wide variety of uses and having a plurality of fluid reservoirs which require the direct filling of fluids into separate reservoirs located within an applicator.

As shown in FIG. 3, housing member 14 comprises a first surface 20 defining a receiving aperture 22, and a second surface 24 forming the exterior of housing member 14 which is integral to the collar 15. The first surface 20 has a proximal portion 26 substantially parallel to the longitudinal axis 28 of the dual filling device 10, a medial portion forming a biasing member 30, and a distal portion forming an angular stop 32. Collar 15 disposes inlet ports 34 and 36 which are adapted to receive the syringe-type applicator 18. Rubber O-rings 38 and 40 are positioned within inlet ports 34 and 36 respectively, such that an air tight seal is formed. Inlet ports 34 and 36 are connected to drawing tubes 42 and 44 by transverse channels 46 and 48 respectively.

Drawing tubes 42 and 44 should have sufficient length to extract substantially all the liquid contained within a container (not shown) positioned within the receiving aperture 22, or conversely they should have a length such that when the system is inverted substantially all of the liquid can be extracted. Drawing tubes 42 and 44 are preferably configured with pointed ends 50 and 52 which have the ability to pierce the protective packaging found on standard medical fluid containers (not shown) and form a seal. Drawing tubes 42 and 44 are preferably formed out of a metallic material, however any suitable material such as thermoplastic may be used. The tubes can also have the ability to be removed from traverse channels 46 and 48 for replacement. Both of the tubes, 42 and 44, may be of similar diameter, however the tube diameter may differ to accommodate liquids having differing viscosities.

Channel 46 allows the fluid contained within an isolated container to be drawn through tube 42 and into the reservoir 19a located within applicator 18 without risk of contamination. Similarly, channel 48 allows the fluid contained within another isolated container to be drawn through tube 44 and deposited within reservoir 19b located within the applicator 18 without risk of contamination. This allows the simultaneous filling of both sides of the applicator directly from the commercially available containers. Channels 46 and 48 can be formed out of thermoplastic tubing or molded directly into body 12 of the direct filling device 10.

Figure 4:
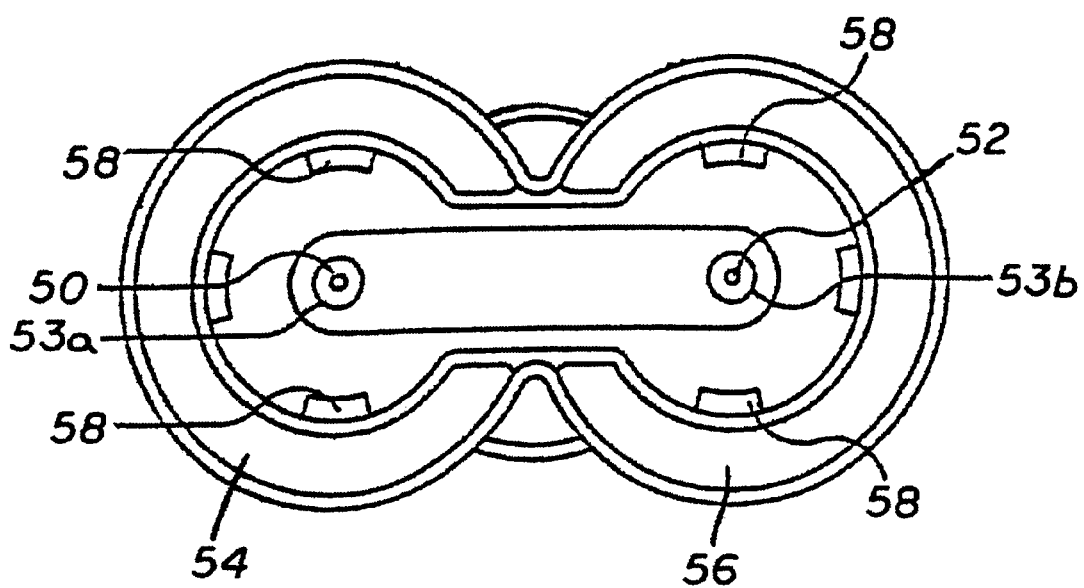
FIG. 4 shows a top view of the container interface of the present invention having two containers disposed within the housing assembly.

As shown in FIG. 4, in order to fill applicator (not shown) directly from containers 54 and 56, housing member (not shown) is placed over said containers 54 and 56 such that pointed tips 50 and 52 are approximately centered on the protective seals 53a and 53b covering the containers. The contoured shape of housing member 14 guides the inventive device as the containers are seated and snap into place within housing member 14 by locking members 58. As shown in FIG. 4, locking members 58 are located within housing member 14 such that they move apart when the caps of the respective containers passes by during the insertion of the container, then once the container has reached the proper location locking members 58 retract under the container caps to lock or "seat" the containers in place.

The plunger of the syringe-type applicator 18 is then retracted thereby drawing the fluid contained within containers 54 and 56, respectively, through their respective drawing tubes 42 and 44 and channels 46 and 48, and into the syringes of applicator 18 for deposit within reservoirs 19a and 19b.

Figure 5:
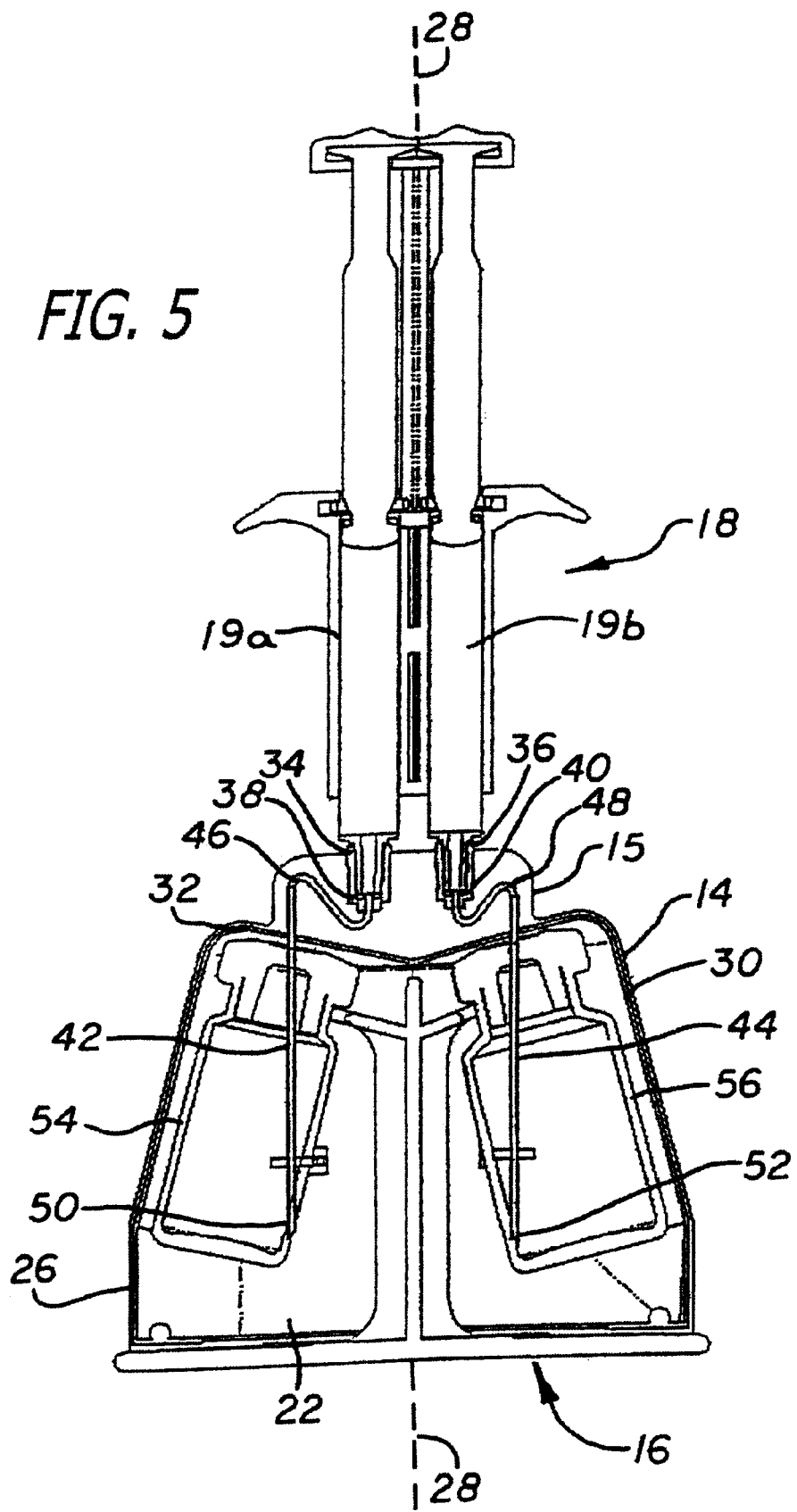
FIG. 5 shows a cross-sectional view of the present invention having two containers disposed within the housing assembly and a syringe-type applicator attached to the device.

As depicted in FIG. 5, containers 54 and 56 are inserted into housing member 14 until seated by locking members 58 (see FIG. 4). The shape of housing member 14 may be varied to allow use of different types and shapes of containers, or alternatively, may be tapered to permit the easy grasp of base 16 when attached to housing member 14, thereby simplifying separation. The housing member 14 and the receiving aperture 22 can also be modified so that each side allows insertion of a different shaped container, thereby keying the containers to the fill device. This in conjunction with the novel shape of the collar is important in ensuring that the proper components are delivered to the proper reservoirs within the applicator. Housing member 14 can be contoured to resemble the shape of the filling device when assembled with agent containers. The shape can also vary to allow use of different types and shapes of containers.

A novel feature of the present invention is the tilted container feature permitting withdrawal of substantially all fluid from agent containers. The angled biasing member 30 forcibly tilts the containers 54 and 56 disposed within the receiving aperture 22, thereby permitting withdrawal of substantially all fluids within the containers. The use of the angular stop member 32 permits an indexed tilting feature while controlling the penetration depth of drawing tubes 42 and 44. In another embodiment housing member 14 may be constructed eliminating the angled biasing member 30 and angular stop 32. The housing member can be modified so that each side allows insertion of a different shaped container, thereby keying the containers to the fill device. This, in conjunction with the novel shape of the collar 15, helps ensure that the proper components are delivered to the proper reservoirs within the applicator.

Figure 6:
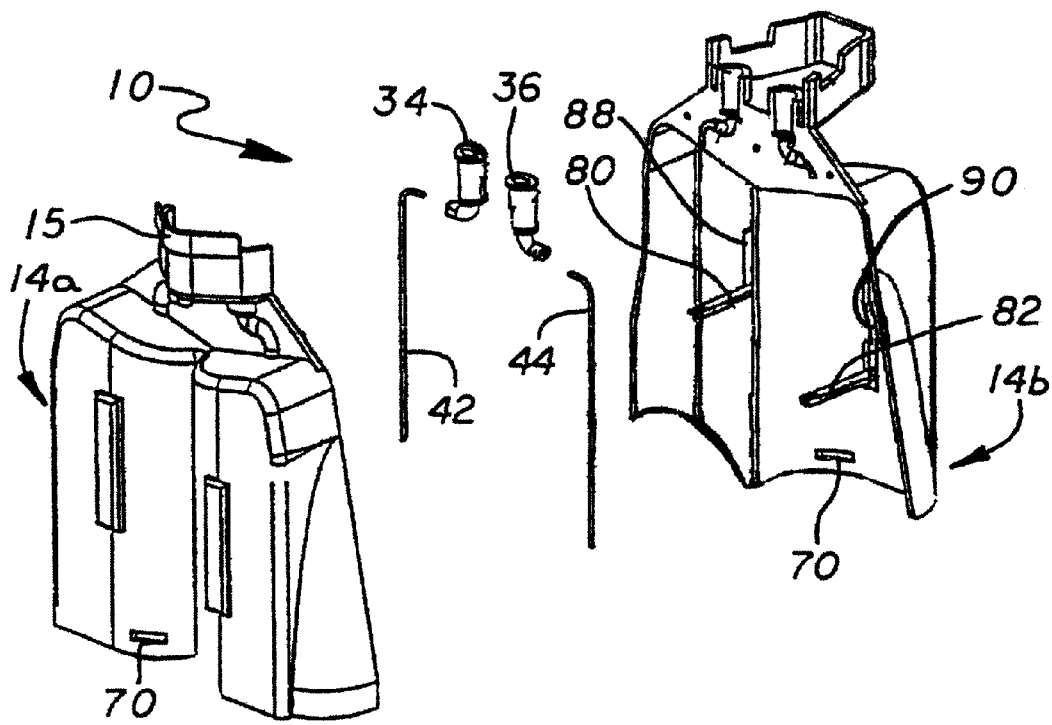
FIG. 6 shows an exploded view of the housing assembly of the present invention.
Figure 7:
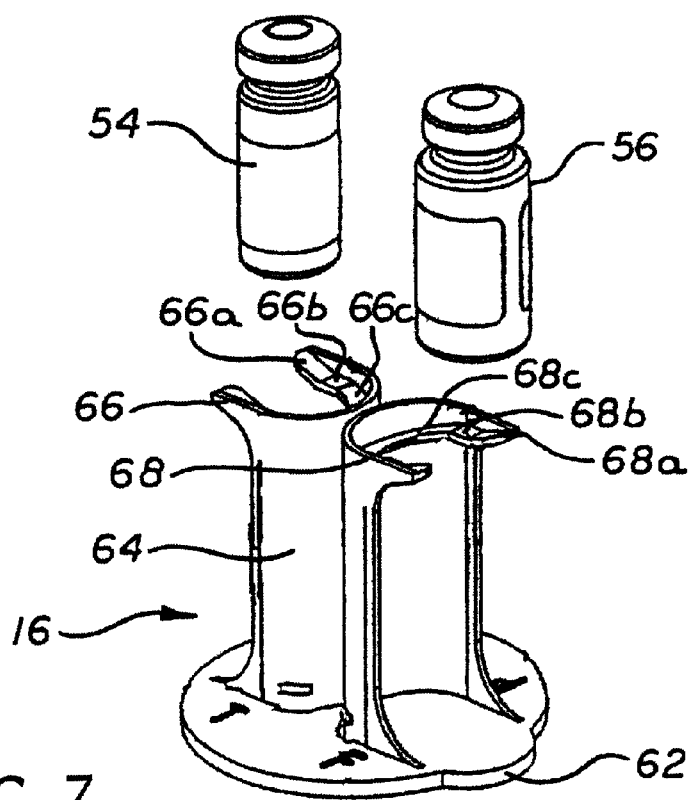
FIG. 7 shows an exploded view of the container positioning members of the present invention.

As shown in FIGS. 6 and 7, the direct dual filling device 10 utilizes a housing member 14, formed of a first housing member portion 14a and a second housing member portion 14b, and base portion 16 to position containers within the receiving aperture 22 (see FIG. 3). Base 16 has base plate portion 62 and a vertical support member 64 disposing at least two angled container supports 66 and 68 to support containers 54 and 56 within the receiving aperture 22. Angling supports 66 and 68 permits tilting of the containers resulting in withdrawal of substantially all the fluid from the container. As shown, the angled supports 66 and 68 may include a medial portion substantially parallel to base plate portion 62, thereby aiding in preparing the device for use. Housing member 14 disposes a sealing base locking member 70 which sealably attaches the base plate portion 62 to the housing member 14. The base locking member 70 may be comprised of retention devices including, without limitation, slip-fit mechanisms, snap-locking mechanisms and pin-locked mechanisms.

An additional embodiment of the present invention includes hinged drawing tube guides 80 and 82 comprising a forked distal portion 84 and 86, respectively, and having the proximal portion attached to the first surface 20 by a hinge device. The hinged drawing tube guides, 80 and 82, respectively, stabilize the drawing tube 42 and 44, respectively, when containers are not placed within the receiving aperture 22. When containers are inserted into the receiving aperture 22 the separate drawing tubes 42 and 44 enter the respective containers 54 and 56, while hinged drawing tube guides 80 and 82 are folded into recesses 88 and 90 disposed on the first surface member 20, thereby permitting complete container insertion.

In preferred embodiments, housing member 14 and base 16 are essentially rigid, injected molded components having limited resilience in their thinner sections. Housing member 14 is also preferably formed from a clear plastic such as polycarbonate or SAN. In contrast, inlets 34 and 36 are preferably fabricated from a distinctly elastomeric, resilient molding material such as silicone rubber.

Housing member 14 and base 16 are configured such that they may only be assembled in one direction, so in use, the operator cannot assemble the device incorrectly. Base 16 and housing member 14 may also color-coded to indicate which side is for the thrombin container in which side is for the fibrinogen container. Furthermore, base 16 may labeled with a "T" indicating the side for thrombin, and an "F" indicating the side for fibrinogen. Once housing member 14 is snapped onto base 16, containers 54 and 56 can be brought into the sterile field.

The assembly of the components of filling device 10 can take place at a factory or other such manufacturing facility prior to use of the inventive device. The housing member 14 generally may be comprised of a first housing member half 14a and a second housing member half 14b, each being molded to dispose the recesses required for fluid channels 46 and 48 and, if required, drawing tube recesses 88 and 90. Drawing tubes 42 and 44 are mated with fluid channels 46 and 48. The assembly is then snugly fitted within the channels formed in the housing member half such that drawing tubes 42 and 44 all are disposed within the void forming one half of the receiving aperture 22. Once the drawing tubes and fluid channels are in place, first-half 14a and second-half 14b, of housing member 14 are configured to be assembled together by snap fit members, thereby forming the receiving aperture 22. Alternatively, ultrasonic welding, glue, press fitting or any other method of assembly may be used. All of the components of the inventive device are then sterilized. When it is desired to use the inventive filling device the operator need only insert the containers and mate the housing member onto the base.

Generally, the agent containers are not sterilized and are unable to be brought into a sterile environment without risk of contamination. However, when the agent containers are shrouded within the inventive filling device the assembly may be brought into a sterile environment for use.

To utilize the present invention, the direct filling device 10, as shown in FIG. 4, is connected to syringe applicator 18. Syringe applicator 18 is placed over the filling device such that the syringes of the applicator are approximately centered over and sealably interact with inlet ports 34 and 36. The novel shaping of the collar 15 allows filling device 10 to mate with syringe applicator 18 in only one orientation, thereby "keying" the fill device to the applicator. The general shape fits to the syringe applicator body in the same manner as interchangeable applicator tips or heads, which are used for droplet or spray dispensing of sealant. Furthermore, the general shape provides a support during the filling device 10 and syringe applicator 18 mating process. The feature of keying the filling device collar 15 to the applicator ensures the proper fibrin components are delivered to their respective reservoirs without significant risk of cross-contamination, particularly when refilling. The collar 15 may be manufactured to functionally attach to a plurality of syringe-type applicators, including without limitation, the DUPLOJECT™ device manufactured by the Baxter Corporation.

The operator then assembles the device by sliding the agent containers 54 and 56 onto horizontal container supports 66 and 68 such that the containers are supported by the necks of the two agent containers. FIG. 7 shows an additional embodiment of the present invention the horizontal angled support comprises a multiple angle planar surface, wherein the horizontal container support surface 66 and 68 comprises a distal portion 66*a* and 68*a* substantially parallel to the angular stop 32, a medial portion 66*b* and 68*b* substantially parallel to base plate portion 62, and a proximal portion 66*c* and 68*c* substantially parallel angular stop 32. The angled distal portions 66*a* and 68*a* and proximal portions 66*c* and 68*c* are angled such that friction will not stop the container from fully seating on level medial portions 66*b* and 68*b*. As stated previously, the bottle supports, generically referred to as 66 and 68, may form a single planar surface. Once the containers are properly seated, the housing member 14 is placed over the base 16. As the housing member 14 is lowered onto the base 16 drawing tubes 42 and 44 pierce the container septum and hinged drawing tube supports 80 and 82 are folded into recesses 88 and 90 formed on the first surface 20. As the housing member 14 is further lowered onto the base 16 the tops of containers 54 and 56 come into contact with the biasing member 30, thereby causing the containers 54 and 56 to tilt. Ideally, the pointed ends, 50 and 52, of the drawing tubes 42 and 44 are shaped such that they conform to the shape of the bottom corner of the agent containers enabling withdrawal of substantially all the agent from the container.

Once the housing member 14 has been completely lowered onto the base 16 into the fully engaged position, it may be locked into place by base locking member 70. Agent containers 54 and 56 are tilted in such a manner that drawing tubes 42 and 44 are forced into the bottom corner of each respective container, which has now become the low point for the agent to pool into. This configuration along with the shaping of the drawing tubes allows for minimal waste of the agent contained within the containers.

Once the inventive filling device is assembled, it may be brought into a sterile field. Although, the agent containers are generally not sterile and therefore would not be allowed within a sterile environment for risk of contamination, the housing member and base assembly has effectively shrouded the containers within a sterile environment so that they may be brought into a sterile field.

Although only two containers are depicted for use with the inventive filling device, adaptation can be easily made to allow the use of one or more containers which can directly fill one or more reservoirs contained within the applicator. This adaptation can be accomplished by decreasing or expanding the housing member and adding or eliminating inlet ports, transverse channels and drawing tubes.

While illustrative embodiments of the invention have been described above, it is, of course, understood that various modifications will be apparent to those of ordinary skill in the art. Many such modifications are contemplated as being within the spirit and scope of the invention.

What is claimed:

1. An apparatus for simultaneously filling at least two dispensing instruments, comprising:
    a housing member having a first surface and a second surface, said first surface forming a inlet aperture;
    a collar member located on said second surface and integral to said housing member;
    at least two inlet port located on said collar member, said at least two inlet ports capable of coupling to syringe-type applicator;
    at least two drawing tubes positioned within said inlet aperture and in communication with said at least two inlet ports; and
    a container positioning member having container support members, said container positioning member receiving at least two material containers within said inlet aperture and said container support members capable of aligning the containers with said drawing tubes.

2. The apparatus of claim 1, wherein said housing member is made from thermoplastic material.

3. An apparatus of claim 2 wherein said thermoplastic is selected form a group consisting of polycarbonate, polystyrene, polypropyene, polytetrafluoroethylene, acrylonitrile butadiene-styrene, and acrylic.

4. The apparatus of claim 1, wherein said housing member comprises a resilient material and sized to permit said housing to conform to said containers disposed therein.

5. The apparatus of claim 1, wherein said first surface comprises:
    a proximal portion substantially parallel to the longitudinal axis of said housing;
    a medial portion forming a biasing surface, said biasing surface having an angular bias towards said housing longitudinal axis thereby forcibly tilting said containers disposed therein; and
    a distal portion forming a angled stop, said angled stop disposed substantially perpendicular to said biasing surface, thereby effectively restricting further advancement of said containers within said inlet aperture and reinforcing said tilting of said containers.

6. An apparatus for simultaneously filling at least two dispensing instruments, comprising:
    a housing member having a first surface and a second surface, said first surface forming a inlet aperture;
    a collar member located on said second surface and integral to said housing member wherein said collar member is attachable to a plurality of dispensing instruments;
    at least two inlet port located on said collar member;
    at least two drawing tubes positioned within said inlet aperture and in communication with said at least two inlet ports; and
    a container positioning member having container support members, said container positioning member receiving at least two material containers within said inlet aperture and said container support members capable of aligning the containers with said drawing tubes. wherein said collar member is attachable to a plurality of dispensing instruments.

7. The apparatus of claim 1, wherein said inlet ports are formed of a flexible sealing elastomer material.

8. The apparatus of claim 1, wherein said collar member further defines at least two material channels in communication with said at least two inlet ports and said at least two drawing tubes, thereby providing a channel in which material may be transported from said at least two drawing tubes to said at least two inlet ports.

9. The apparatus of claim 1, wherein said at least two drawing tubes have a proximal portion attachable to said material channel and a distal portion located within said inlet aperture.

10. The apparatus of claim 9, wherein said at least two drawing tubes have pointed tips to pierce and sealably interface with said containers.

11. An apparatus for simultaneously filling at least two dispensing instruments, comprising:
    a housing member having a first surface and a second surface, said first surface forming a inlet aperture;
    a collar member located on said second surface and integral to said housing member;

at least two inlet port located on said collar member;

at least two drawing tubes positioned within said inlet aperture and in communication with said at least two inlet ports;

at least two hinged support members having a proximal portion attached to said first surface of said housing member in a hinged fashion, and a distal portion enabling supportive interaction of said at least two hinged support members and said at least two drawing tubes; wherein said at least two hinged support members support said at least two drawing tubes absent said containers disposed within said inlet aperture; and a container positioning member having container support members, said container positioning member receiving at least two material containers within said inlet aperture and said container support members capable of aligning the containers with said drawing tubes.

12. An apparatus for simultaneously filling at least two dispensing instruments, comprising:

a housing member having a first surface and a second surface, said first surface forming a inlet aperture;

a collar member located on said second surface and integral to said housing member;

at least two inlet port located on said collar member;

at least two drawing tubes positioned within said inlet aperture and in communication with said at least two inlet ports;

at least two hinged support members having a proximal portion attached to said first surface of said housing member in a hinged fashion, and a distal portion enabling supportive interaction of said at least two hinged support members and said at least two drawing tubes; wherein said at least two hinged support members support said at least two drawing tubes absent said containers disposed within said inlet aperture, wherein the distal portion of said at two hinged support members are forked; and a container positioning member having container support members, said container positioning member receiving at least two material containers within said inlet aperture and said container support members capable of aligning the containers with said drawing tubes.

13. The apparatus of claim 1, wherein said container positioning member comprises a base plate portion capable of securely positioning said material containers within said inlet aperture aligned with said at least two tubes, thereby permitting withdrawal of material form said containers by said at least two drawing tubes.

14. The apparatus of claim 13, further comprising:

a vertical support member attached to said base plate portion;

at least one angled support member having a proximal portion connected to said vertical support member and a distal portion defining an opening;

said opening being substantially aligned with said at least two drawing tubes and capable of receiving and supporting said containers, thereby permitting said at least two drawing tubes to withdrawal fluid from said containers.

15. The apparatus of claim 14, wherein said at least one angled support member has an angled distal portion, a substantially level medial portion, and a proximal portion substantially parallel to said distal portion, thereby permitting tilting of said containers.

16. The apparatus of claim 1, wherein said container positioning member lockably interacts with said housing member.

17. The apparatus of claim 16, wherein said locking mechanism is a snap lock disposed on said housing member.

18. The apparatus of claim 16, wherein said locking mechanism is a slip-fit lock disposed on said housing member.

19. The apparatus of claim 16, wherein said locking interaction sealably positions said containers within said housing member.

20. The apparatus of claim 1, wherein said container positioning member is made from thermoplastic material.

21. The apparatus of claim 20, wherein said thermoplastic is selected form a group consisting of polycarbonate, polystyrene, polypropyene, polytetrafluoroethylene, acrylonitrile butadiene-styrene, and acrylic.

* * * * *